(12) United States Patent
Inoue et al.

(10) Patent No.: US 9,743,879 B2
(45) Date of Patent: Aug. 29, 2017

(54) KINEMATIC ANALYSIS BASED ON MRI BONE MARROW SIGNALS

(71) Applicant: Rush University Medical Center, Chicago, IL (US)

(72) Inventors: Nozomu Inoue, Chicago, IL (US); Alejandro A. Espinoza Orias, Chicago, IL (US)

(73) Assignee: Rush University Medical Center, Chicago, IL (US)

( * ) Notice: Subject to any disclaimer, the term of this patent is extended or adjusted under 35 U.S.C. 154(b) by 0 days.

(21) Appl. No.: 14/861,773

(22) Filed: Sep. 22, 2015

(65) Prior Publication Data

US 2016/0093093 A1   Mar. 31, 2016

Related U.S. Application Data

(60) Provisional application No. 62/056,135, filed on Sep. 26, 2014.

(51) Int. Cl.

| | |
|---|---|
| *A61B 5/00* | (2006.01) |
| *A61B 5/11* | (2006.01) |
| *A61B 5/055* | (2006.01) |
| *G06T 7/33* | (2017.01) |
| *G06T 7/246* | (2017.01) |

(52) U.S. Cl.
CPC ............ *A61B 5/4585* (2013.01); *A61B 5/055* (2013.01); *A61B 5/1128* (2013.01); *A61B 5/4504* (2013.01); *A61B 5/458* (2013.01); *A61B 5/459* (2013.01); *A61B 5/4566* (2013.01); *A61B 5/4571* (2013.01); *A61B 5/4576* (2013.01); *A61B 5/4595* (2013.01); *G06T 7/248* (2017.01); *G06T 7/337* (2017.01); *G06T 2200/04* (2013.01); *G06T 2207/10088* (2013.01); *G06T 2207/30012* (2013.01)

(58) Field of Classification Search
USPC .................................................. 382/128-134
See application file for complete search history.

(56) References Cited

U.S. PATENT DOCUMENTS

| | | | |
|---|---|---|---|
| 2002/0177770 A1* | 11/2002 | Lang ................ | A61B 5/055 600/410 |
| 2013/0230224 A1* | 9/2013 | Claude ............. | A61B 5/055 382/131 |

OTHER PUBLICATIONS

Fujiwara MD, A et al.; "The Effect of Disc Degeneration and Facet Joint Osteoarthritis on the Segmental Flexibility of the Lumbar Spine";SPINE, vol. 25, No. 23; Dec. 1, 2000; pp. 3036-3044.

Ochia, R et al.; "In Vivo Measurements of Lumbar Segmental Motion During Axial Rotation in Asymptomatic and Chronic Low Back Pain Male Subjects"; SPINE, vol. 3, No. 13; Jun. 1, 2007; pp. 1394-1399.

(Continued)

*Primary Examiner* — Alex Liew
(74) *Attorney, Agent, or Firm* — Brinks Gilson & Lione

(57) ABSTRACT

A method of a measuring kinematic parameter in a subject is provided. The method includes obtaining a first magnetic resonance (MR) image set of a bone marrow segment of the subject in a first position and obtaining a second MR image set of the bone marrow segment of the subject in a second position where the second position different from the first position. The method further includes registering the first image set with the second image set and measuring a kinematic parameter.

4 Claims, 6 Drawing Sheets

(56) References Cited

OTHER PUBLICATIONS

Ochia, R et al.; "Three-Dimensional In Vivo Measurement of Lumbar Spine Segmental Motion"; SPINE, vol. 31, No. 18; Aug. 15, 2006; pp. 2073-2078.

Watanabe, S et al.; "Three-dimensional kinematic analysis of the cervical spine after anterior cervical decompression and fusion at an adjacent level: a preliminary report"; Eur Spine J, vol. 21, Issue 5; May 2012 pp. 946-955.

Kitahata, S et al.; "A New MRI-Based Bone-marrow Model for In Vivo Spine Kinematics"; ORS 2015 Annual Meeting, Mar. 28-31, 2015; Abstract.

Kitahata, S et al.; "In Vivo Kinematic Analysis of the Spine using a 3D MRI Bone-marrow Model"; presented at the ISTA 27$^{th}$ Annual Congress in Kyoto Japan, Sep. 24-27, 2014.

\* cited by examiner 3D-3D Registration

-1.5 mm (shrinkage)    Original    +1.5 mm (expansion)

+0.3 mm expansion

Top view

Right                    Left

KINEMATIC ANALYSIS BASED ON MRI BONE MARROW SIGNALS

RELATED APPLICATIONS

This application claims the benefit of U.S. Provisional Application No. 62/056,135, filed Sep. 26, 2014, which is incorporated by reference herein in its entirety.

FEDERALLY SPONSORED RESEARCH OR DEVELOPMENT

This invention was made with Government support under Grant No. R01 AT006692-01A1, awarded by the National Institutes of Health, National Center for Complementary and Alternative Medicine. The Government has certain rights in the invention.

TECHNICAL FIELD

The present invention relates generally to a non-invasive method for measuring kinematic parameters in a subject, and more particularly to a method using magnetic resonance imaging (MRI) of bone marrow to measure kinematic parameters in a subject.

BACKGROUND

Spinal instability has been implicated as a cause of low back pain, and it can usually be assessed by studying motion. Kinematic analyses of the spine have been recognized as an effective method for functional examination of the spine and its disorders helping to understand in-vivo 3D spinal mechanics. Imaging modalities such as Computed Tomography (CT) and MRI are suitable to obtain vertebral geometry. However, radiation is a clinical concern associated with CT and while MRI is noninvasive, detection of bone edges especially at endplates and processes where soft tissues attach, is usually difficult. For both methods, the range of motion possible is commonly restricted to motion along or about the longitudinal axis of the body, making it ideal for torso rotation, as these methods constrain the body within the bore of the CT or MRI scanner. An added advantage of both imaging modalities is that they are able to capture images of large bones and organs that in the case of bony structures can be assumed to behave as rigid bodies, which is required to study kinematics. However, bone exterior contours are not always necessary for kinematics analysis of the segments of the body such as the spine, hip, knee, ankle, foot, hand, wrist and shoulder as long as the image shows consistent landmarks between imaging positions.

What is needed in the art is a non-invasive, reliable and robust method for kinematic analysis of segments of the body using an MRI-based bone-marrow model.

BRIEF SUMMARY

In one aspect, a method of a measuring kinematic parameter in a subject is provided. The method includes obtaining a first magnetic resonance (MR) image set of a bone marrow segment of the subject in a first position and obtaining a second MR image set of the bone marrow segment of the subject in a second position where the second position different from the first position. The method further includes registering the first image set with the second image set and measuring a kinematic parameter.

In another aspect, a method of measuring a kinematic parameter in a subject is provided. The method includes obtaining a first magnetic resonance (MR) image set of a first bone marrow segment of the subject in a first position and obtaining a second MR image set of the first bone marrow segment of the subject in a second position, the second position different from the first position. The method also includes obtaining a first MR image set of a second bone marrow segment of the subject in the first position and obtaining a second MR image set of the second bone marrow segment of the subject in the second position. The method further includes registering the first image set with the second image set of the first bone marrow segment, registering the first image set with the second image set of the second bone marrow segment and measuring a kinematic parameter for the first bone marrow segment relative to the second bone marrow segment.

Figure 1:
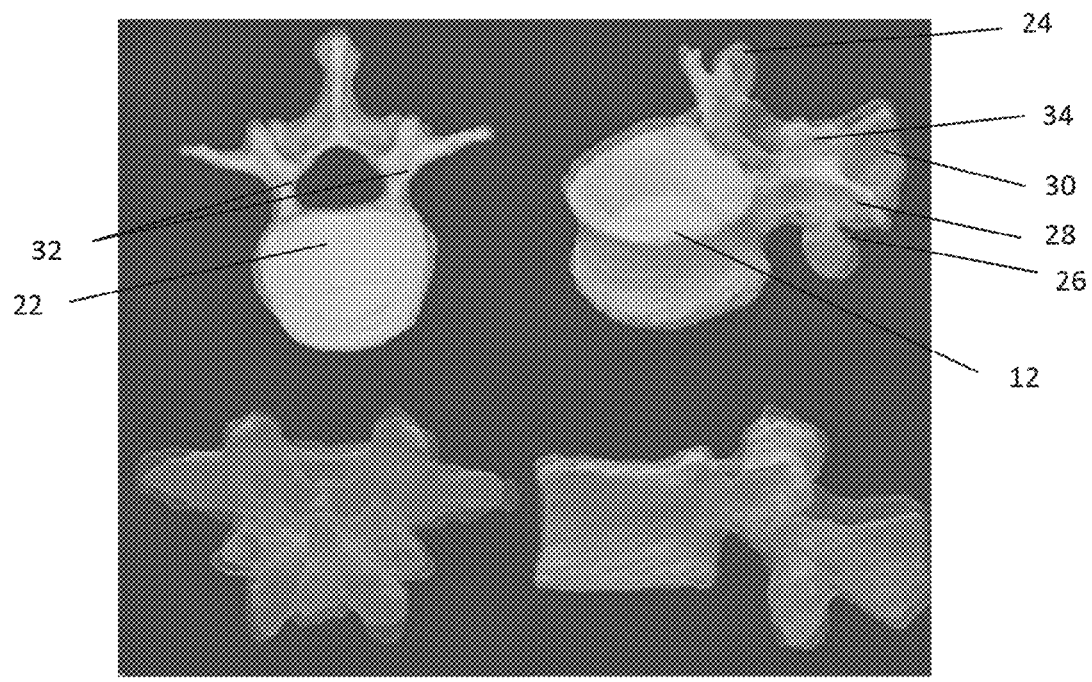
FIG. 1 illustrates an MRI bone marrow model overlaid with a CT bone model.

Advantages of the present invention will become more apparent to those skilled in the art from the following description of the preferred embodiments of the present invention that have been shown and described by way of illustration. As will be realized, the invention is capable of other and different embodiments, and its details are capable of modification in various respects. Accordingly, the drawings and description are to be regarded as illustrative in nature and not as restrictive.

DETAILED DESCRIPTION

The present invention provides methods for kinematic analysis using an MRI-based bone marrow model.

Kinematic Analysis

Kinematic analysis is used to describe the motion of points and/or solid bodies. Kinematic analysis of joints and other body structures has been recognized as an effective method for functional analysis of the joints and other body structures and relies on tracing of rigid bodies. Kinematic analysis may be used to investigate many types of movement by a subject depending on the portion of the body to be analyzed. In some embodiments, the kinematic analysis may include rotational movement and translational movement. As shown herein, kinematic analysis may be used without incorporating bony geometry and may be used with bone marrow images.

MRI

MRI has been widely applied in medical fields. Typically, MRI produces an image of a part of an object under examination by manipulating the magnetic spins and processing measured responses from the magnetic spins. An MRI system can include hardware to generate different magnetic fields for imaging, including a static magnetic field along a z-direction to polarize the magnetic spins and gradient fields along mutually orthogonal x, y, or z directions to spatially select a body part for imaging, as well as hardware to generate a radiofrequency (RF) field to manipulate the spins. Software is also commercially available to provide segmentation of the images and to create two-dimensional and three dimensional models. However, bony models typically used for kinematic analysis are difficult to create using MRI due to the low intensity of bony structure images.

Bone marrow is readily imagable using MRI. The interface between the bone marrow and the bone provides a model of the internal structure of the bone rather than the external structure of the bone. The interface can be easily and consistently detected due to the high-contrast interface MRI intensity. In some embodiments, T1 or T2 MR images may be used. Any site within a subject that includes a bone marrow component may be used for kinematic analysis using the MRI-based bone marrow model described herein. By way of non-limiting example, bone marrow MRI images may be obtained from the spine, hand, wrist, foot, ankle, hip, shoulder and knee. In some embodiments, the kinematic analysis may be performed with respect to two vertebrae in the spinal column of the subject.

Methods of Kinematic Analysis

Methods of the present invention include kinematic analysis using MRI images of bone marrow. The method includes obtaining MR image sets. Any type of MR imaging system that is used in a clinical setting may be used to obtain the MR image sets. By way of non-limiting example, T1 or T2 images may be obtained. Other suitable images may also be used that provide a sufficiently clear border against the bony tissue surrounding the bone marrow. Aspects of the present invention will be described with reference to the spine of the subject, however, the present invention may also be used with bone marrow images from the hip, knee, ankle, foot, hand, wrist and shoulder and the like. In some embodiments, two sets of images may be obtained for a bone marrow segment, each set in a different position. In some embodiments, three or four sets of images may be obtained for a bone marrow segment, each set in a different position. In some embodiments, two or more sets of images may be obtained for a bone marrow segments each set in a different position.

Figure 2:
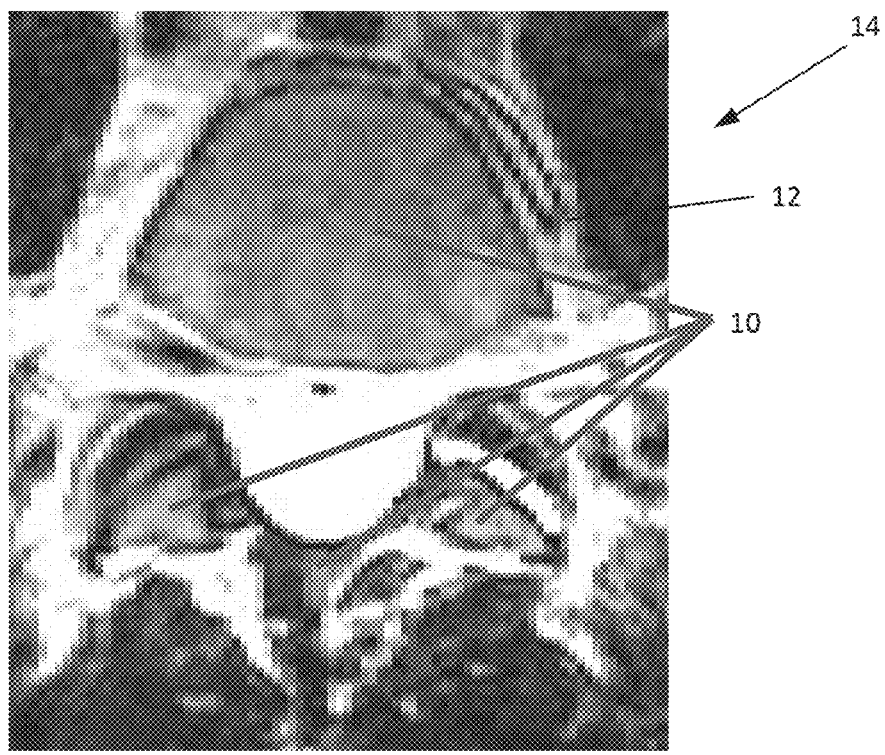
FIG. 2 illustrates section of a bone marrow segment of a spinal section.

FIG. 2 illustrates bone marrow segments 10 that are viewable using MR imaging of a spinal segment 12 in a section 14 of an image set. Different segments of bone marrow within an image may be used for the kinematic analysis. For example, as shown in FIGS. 1 and 2, spinal bone marrow segments 10 from the vertebral body 22, the superior process(es) 24, the inferior process(es) 26, the transverse process 28, the spinous process 30, pedicles 32 and/or laminae 34 may be used. In some embodiments, the bone marrow segment 12 from the vertebral body 22 may be used to obtain the MR image sets. In some embodiments, bone marrow segments 12 may be used from the vertebral body 22 in combination with one, two, three, four, five or six of the bone marrow segments 12 selected from the superior process(es) 24, the inferior process(es) 26, the transverse process 28, the spinous process 30, pedicles 32 and laminae 34. In some embodiments, the superior process(es) 24, the inferior process(es) 26, the transverse process 28, the spinous process 30, pedicles 32 or laminae 34 may be used singularly or in combination with one or more of the group consisting of the superior process(es) 24, the inferior process(es) 26, the transverse process 28, the spinous process 30, pedicles 32 and laminae 34.

Figure 3A:
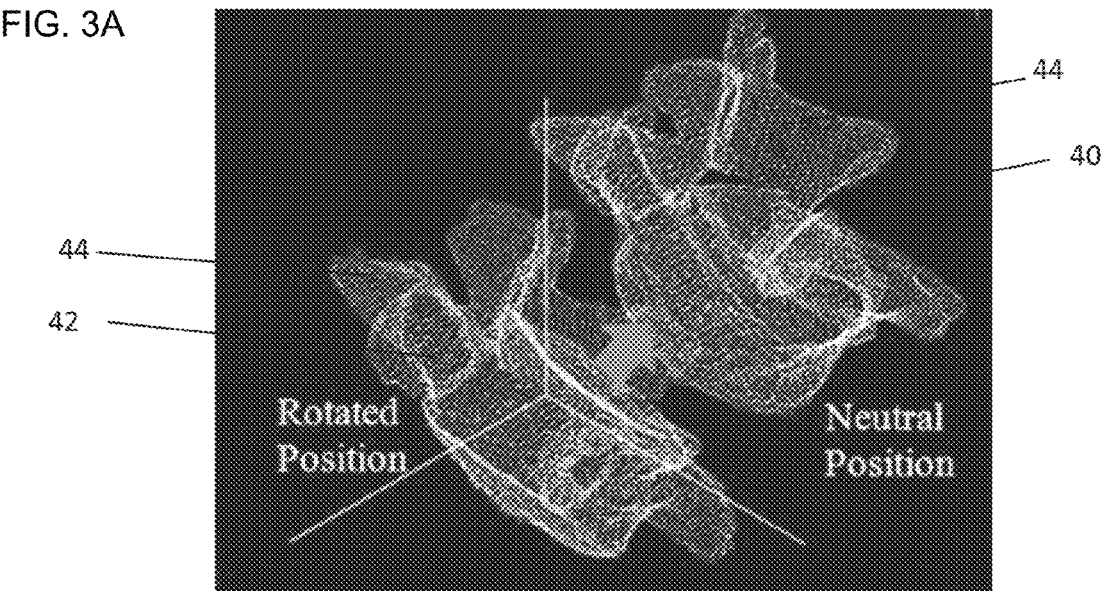
FIG. 3A illustrates models in a first position and a second positon.
Figure 3B:
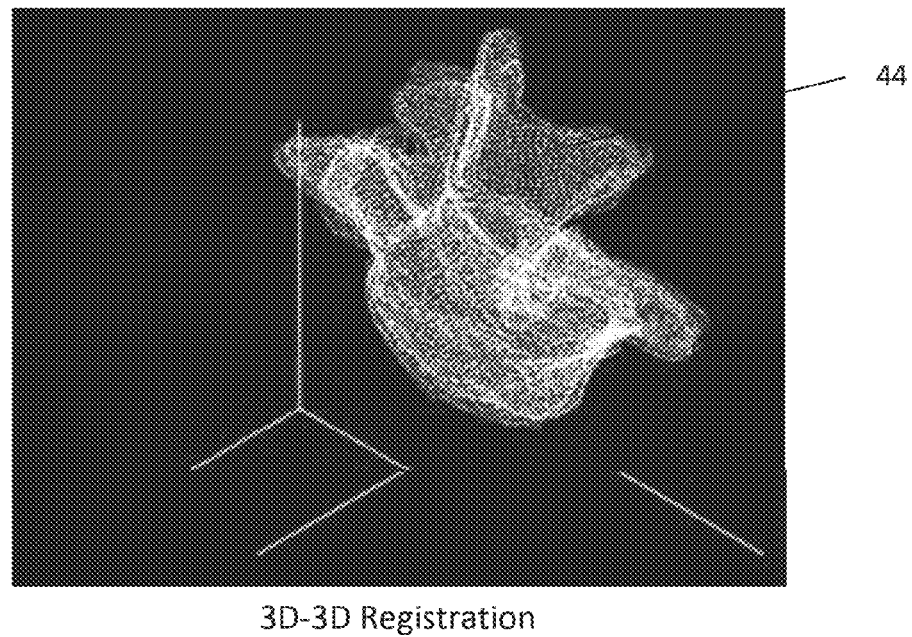
FIG. 3B illustrates the registration of the models from FIG. 3A.

According to an embodiment of the present invention, a first MR image set is obtained of a bone marrow segment 12 of the subject in a first position 40. The first position 40 may be a neutral position. A second MR image is obtained is obtained of a bone marrow segment 12 of the subject in a second position 42. The second position 42 may be a rotated position or a translated position. In some embodiments, models 44 of the first and second MR image sets may be made as shown in FIG. 3A. Commercially available software may be used to create the models. By way of non-limiting example, software from Mimics, Materialise, Leuven, Belgium may be used. The models 44 may be two-dimensional models or three-dimensional models. The models 44 in the first position 40 and the second position 42 may be registered by moving the model 44 of the first position 40 toward the model 44 of the second position 42. Alternatively, the model 44 of the second position 42 may be moved toward the model 44 of the first position 40 as shown in FIG. 3A. The registered models 44 are shown in FIG. 3B.

Figure 4:
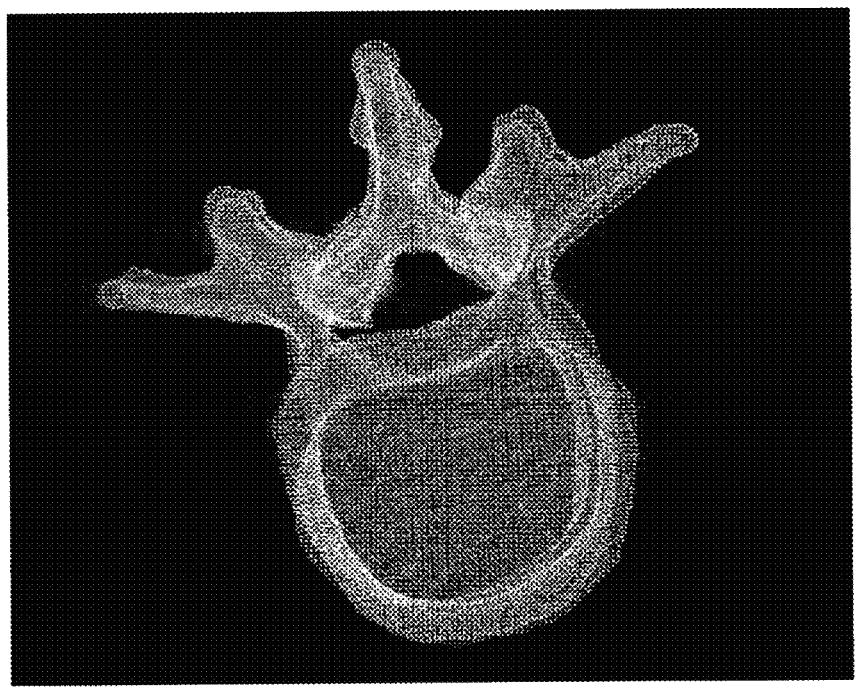
FIG. 4 illustrates a registration of models having different volumes.
Figure 5:
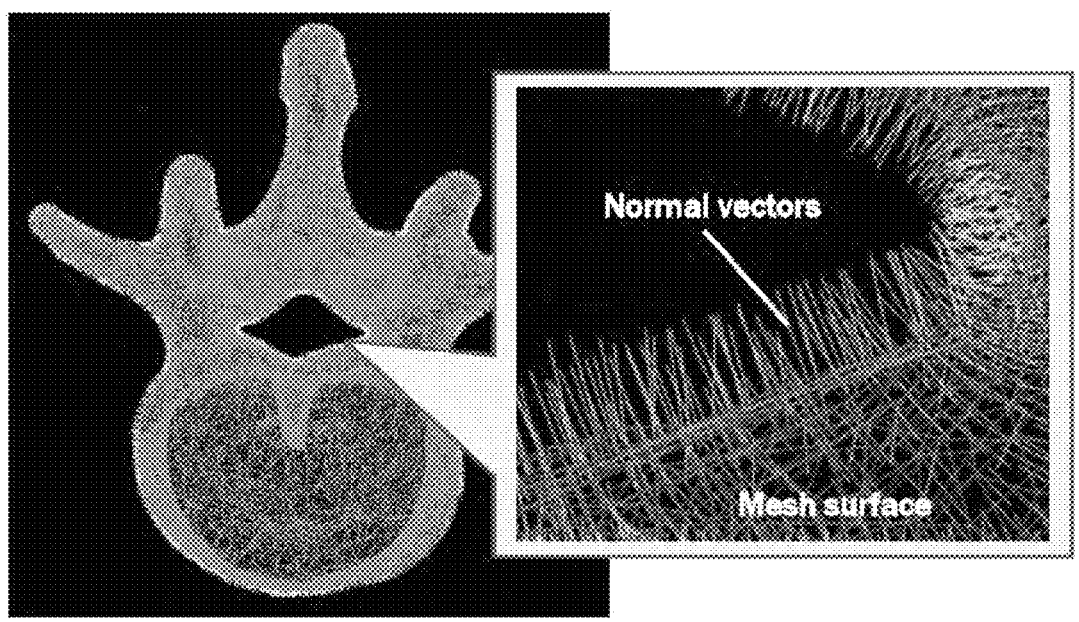
FIG. 5 illustrates normal vectors that are generated for volume adjustment of the model.
Figure 6:
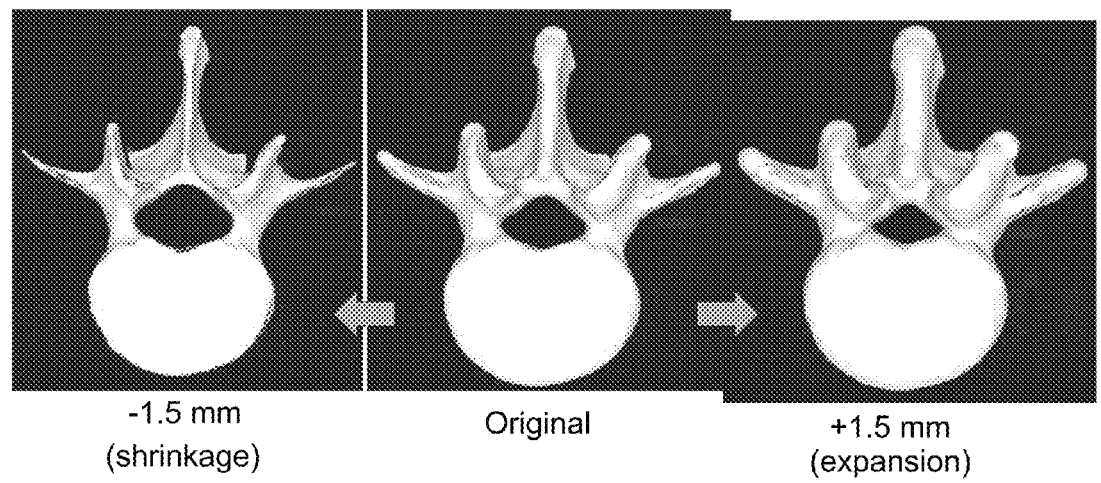
FIG. 6 illustrates shrinkage and expansion of the original model.
Figure 7:
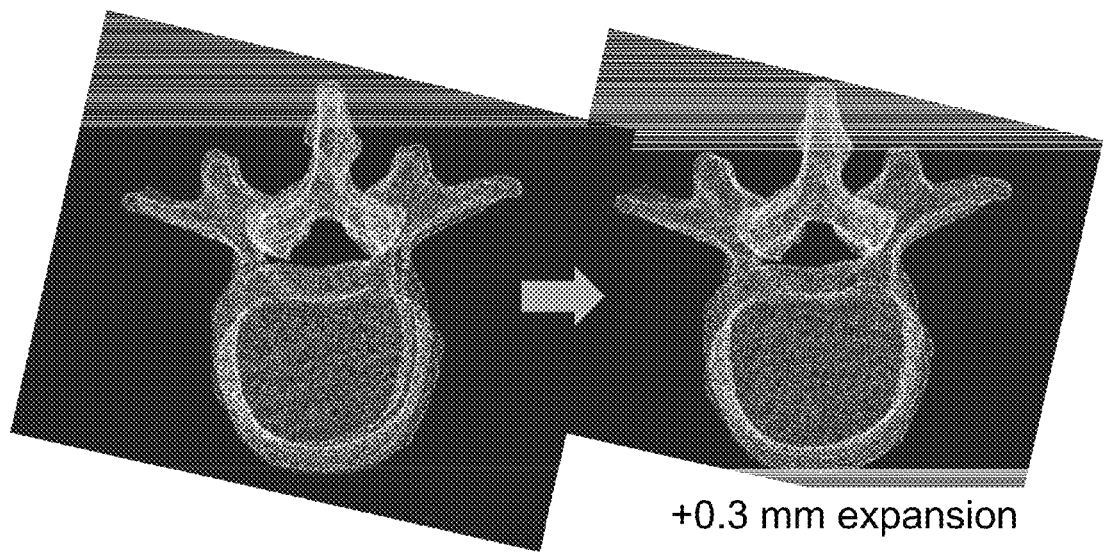
FIG. 7 illustrates the volume adjustment of the models, unadjusted (left) and volume adjusted (right)

In some embodiments, the models 44 may need to be volume adjusted to have the model 44 of the first position 40 the same size as the model 44 of the second position 42. The size difference between the models 44 is caused by differences in signal intensity of the MRI system. FIG. 4 illustrates registered image with two different sized models 44. FIG. 5 illustrates an example of volume adjustment. In some embodiments, individual mesh element normal vectors may be obtained. Each point of the model 44 may be moved outward or inward in a direction parallel to the normal vector to resize one or both models 44. FIG. 6 illustrates the volume adjustment showing both shrinkage (left) and expansion (right) of the original model 44. FIG. 7 illustrates the results of the volume adjustment comparing the unadjusted models 44 on the left with the volume adjusted models on the right. The registration procedure described above may be performed after one or both models are volume adjusted.

Figure 8:
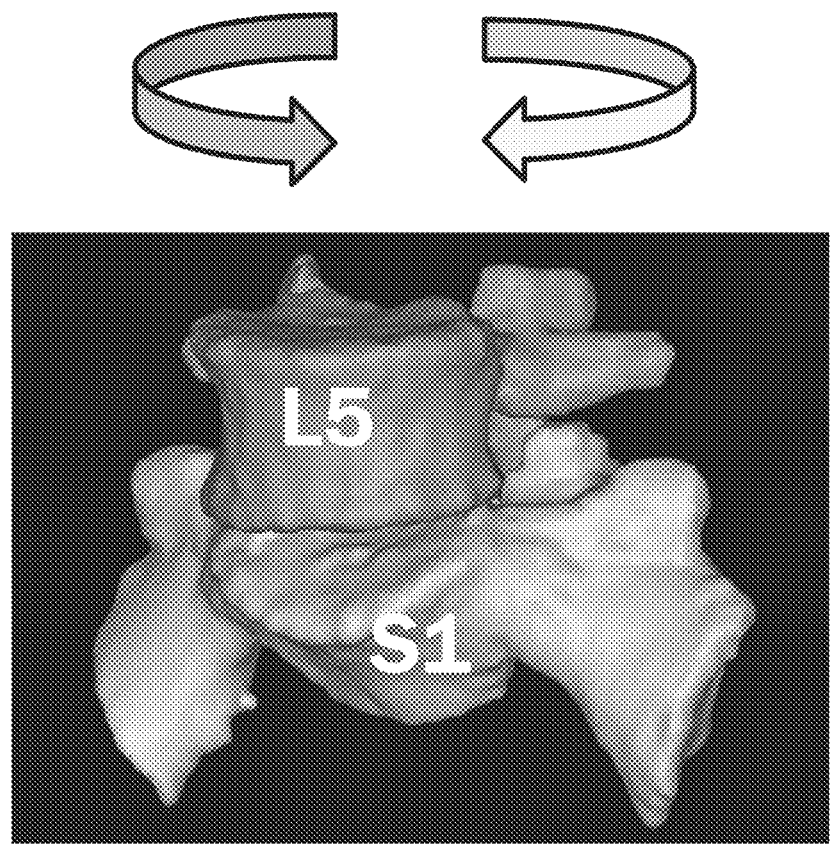
FIGS. 8 and 9 illustrate an example of one of the kinematic parameters measurable according the methods of the present invention.
Figure 9:
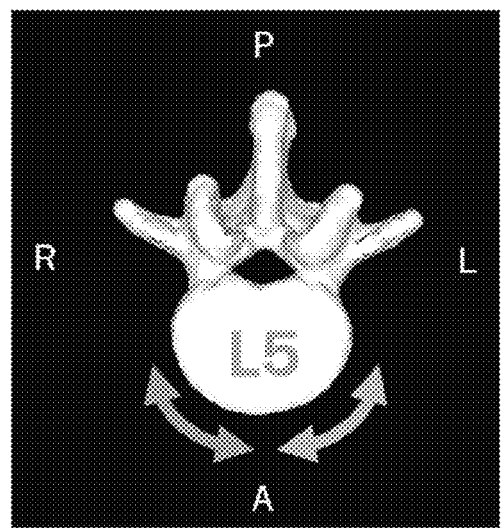

FIGS. 8 and 9 illustrate exemplary kinematic parameters that may be measured using the methods described herein. By way of non-limiting example, FIGS. 8 and 9 show axial rotation.

EXAMPLE

Methods

An IRB-approved study recruited 17 patients undergoing lumbar decompression surgery to treat a single-level symptomatic herniation as part of a clinical trial for a new dynamic stabilization device (not discussed with reference to the present invention). T1 & T2 sagittal 3T MRI scans (Magnetom Skyra, Siemens, Erlangen, Germany) were acquired as part of the pre-operative evaluation in three positions: supine and with the shoulders rotated 45° to the left and right to induce torsion of the lumbar spine by means of a bolster pillow. The MRI scans were used for evaluation of bone marrow models for kinematic analysis.

Commercially-available medical segmentation software (Mimics, Materialise, Leuven, Belgium) was used to create 3D bone-marrow models of L5 and S1 at the neutral and rotated positions by selecting a threshold level of the bone-marrow intensity at the bone-marrow/bone interface. Bone-marrow models were created from the vertebral corpus. Bone marrow models were also created from the superior/inferior, transverse and spinous processes, pedicles and laminae. One or more of the bone marrow models created from the vertebral corpus, the superior/inferior, transverse and spinous processes, pedicles and laminae may be used in order to have consistent landmarks in the rotation analysis. (See FIG. 1)

Kinematics Analysis

Figure 10A:
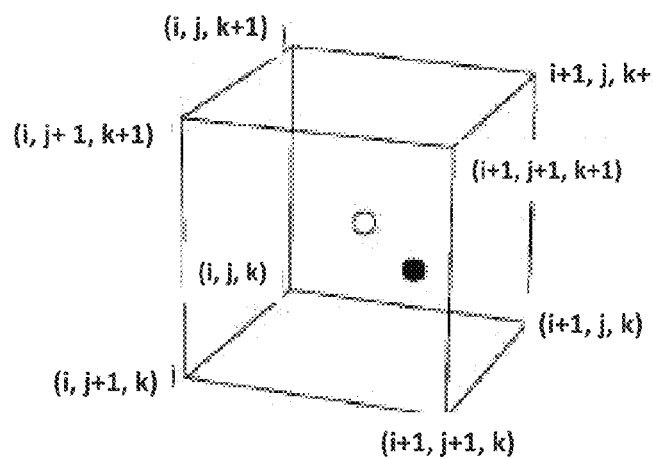
FIGS. 10A and 10B illustrate a voxel created for each stationary target vertebra point (○). For percentage of volume merging calculation, a voxel, which included a point from the moving vertebra (●), was counted (10A). Otherwise it was not counted when the point of the moving vertebra (●) was located outside of the voxel (10B). The i, j, and k are integer values for the voxel coordinates.
Figure 10B:
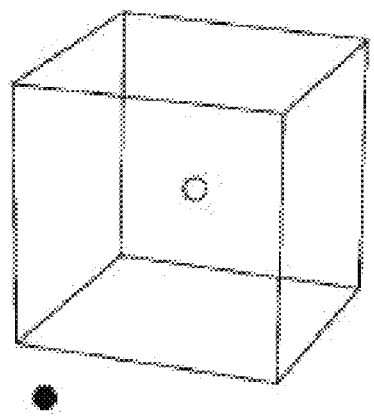

Segmental motions in 6 degree-of-freedom at L5/S1 were measured by using the validated Volume-Merge method as a 3D-3D registration technique. The Volume-Merge method was implemented through a custom-written software program in Visual C++ 2003 under Microsoft Foundation Class programming environment (Microsoft, Redmond Wash.). In the volume merge method, a vertebral body in the neutral position (the moving vertebra) was virtually rotated and translated toward the same body in a rotated position (the stationary target). These rotations and translations of the vertebral body were conducted with 0.1° and 0.1 mm increments, respectively, until the moving vertebra merged with the stationary target in the rotated position. The degree of volume merging was maximized in real-time through rotation or translation of the moving vertebra using the following algorithm. A voxel with a dimension of 1.0×1.0×1.0 mm was created for each point of the stationary target. The number of points of the moving vertebra that fell within the voxel of the stationary target was determined, and the percentage of volume merge was defined by the following formula (Equation 1 and FIG. 10):

$$\text{Percentage of volume merge:} = \frac{\text{number of voxels including the moving vertebra points}}{\text{total number of voxels of the stationary target}}$$

When size differences between the bone-marrow models in different positions were noted, the following volume adjustment was performed: Each point consisting of the bone-marrow model was moved outwards or inwards in a direction parallel to the normal vector of each polygon surface mesh element with an increment of 0.1 mm. The Volume-Merge procedure was performed after the volume adjustment was applied. This procedure was repeated until the best 3D-3D registration was obtained.

Results

Based on the bone-marrow models, angular kinematics were analyzed: Segmental rotation (mean±SD) at the L5/S1 level was shown to be symmetric for both left and right motions (p=0.149); Left: 1.04°±0.93° and Right: 1.33°±0.80°. The range of motion recorded was: left [0.05°-3.70°] and right [0.35°-3.25°]. These values were equivalent to previously reported values of axial lumbar rotation measured by 3D CT lumbar models. (Ochia et al., Three-dimensional in vivo measurement of lumbar spine segmental motion. Spine (Phila Pa. 1976) 2006 Aug. 15; 31(18):2073-8.)

This study demonstrated feasibility of kinematic analyses using the 3D bone-marrow model created with clinical MRI. The bone-marrow model shows the bone-marrow/bone interface geometry—the internal structure of the vertebra rather than outside geometry usually used for kinematic analyses—that is easily and consistently detected due to its high-contrast interface MRI intensity, which does not require lengthy manual tracing of the bony contour. The bone-marrow model includes key elements of the vertebra including posterior elements and the 3D-3D registration technique used for 3D-CT model can be applied (FIG. 1). This type of methodology can be used in the clinic to evaluate with sufficient accuracy subject-specific spinal kinematics without exposure to additional radiation. The MRI-based 3D bone-marrow model may also be useful for kinematic analyses of other major joints such as hip, knee, ankle, foot, hand, wrist and shoulder joints.

The above Figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims.

The invention claimed is:

1. A method of measuring a kinematic parameter in a subject, the method comprising:
    obtaining a first magnetic resonance (MR) image set of a bone marrow segment of the subject in a first position;
    obtaining a second MR image set of the bone marrow segment of the subject in a second position, the second position different from the first position;
    making a first model of the first MR image set and a second model of the second MR image set;
    volume adjusting the models to remove size differences between the models of the first and second MR image sets before registering the models;
    obtaining an individual mesh element normal vector for the first and/or the second models and moving each point of the model in a direction parallel to the individual mesh element normal vector to adjust the volume;
    registering the models; and
    measuring a kinematic parameter.

2. A method of measuring a kinematic parameter in a subject, the method comprising:
    obtaining a first magnetic resonance (MR) image set of a first bone marrow segment of the subject in a first position;
    obtaining a second MR image set of the first bone marrow segment of the subject in a second position, the second position different from the first position;
    registering the first MR image set with the second MR image set of the first bone marrow segment;
    obtaining a first MR image set of a second bone marrow segment of the subject in the first position;
    obtaining a second MR image set of the second bone marrow segment of the subject in the second position;
    registering the first MR image set with the second MR image set of the second bone marrow segment; and
    measuring a kinematic parameter for the first bone marrow segment relative to the second bone marrow segment.

3. The method according to claim 2, wherein the first bone marrow segment is from a first vertebra and the second bone marrow segment is from a second vertebra.

4. The method according to claim 3, wherein the first and second vertebrae are adjacent to each other in a spinal column of the subject.

* * * * *